US012773101B2

(12) United States Patent
Giuliani

(10) Patent No.: US 12,773,101 B2
(45) Date of Patent: Oct. 27, 2026

(54) ABLATING APPARATUS

(71) Applicant: Alleima Karlsruhe GmbH, Karlsruhe (DE)

(72) Inventor: Laura Giuliani, Varese (IT)

(73) Assignee: Alleima Karlsruhe GmbH, Karlsruhe (DE)

( * ) Notice: Subject to any disclaimer, the term of this patent is extended or adjusted under 35 U.S.C. 154(b) by 129 days.

(21) Appl. No.: 18/714,442

(22) PCT Filed: Nov. 30, 2022

(86) PCT No.: PCT/EP2022/083888
§ 371 (c)(1),
(2) Date: May 29, 2024

(87) PCT Pub. No.: WO2023/099582
PCT Pub. Date: Jun. 8, 2023

(65) Prior Publication Data

US 2025/0017452 A1 Jan. 16, 2025

Related U.S. Application Data

(60) Provisional application No. 63/335,786, filed on Apr. 28, 2022.

(30) Foreign Application Priority Data

Dec. 1, 2021 (IT) ........................ 102021000030410

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00133* (2013.01); *A61B 1/267* (2013.01); *A61B 1/273* (2013.01)

(58) Field of Classification Search
CPC ..... A61B 1/018; A61B 1/00133; A61B 1/267; A61B 1/273; A61B 2018/00196; A61B 2018/00279; A61B 2018/00982
See application file for complete search history.

(56) References Cited

U.S. PATENT DOCUMENTS 4,946,440 A * 8/1990 Hall .................. A61M 16/0833 606/7
5,259,366 A * 11/1993 Reydel ................ A61B 17/221 383/203

(Continued)

FOREIGN PATENT DOCUMENTS

EP 3122233 B1 10/2018
WO 2018/033910 A1 2/2018

OTHER PUBLICATIONS

International Search Report and Written Opinion dated Mar. 21, 2023, issued in corresponding International Patent Application No. PCT/EP2022/083888.

(Continued)

*Primary Examiner* — Anh Tuan T Nguyen
*Assistant Examiner* — Jae Woo
(74) *Attorney, Agent, or Firm* — Morgan, Lewis & Bockius LLP

(57) ABSTRACT

Medical apparatus supports and centers a treatment device treating internal walls of a longitudinal cavity, in particular a human cavity, has a longitudinal sheath insertable in a working channel of an endoscopic device; and a positioning element with a first end connectable to the longitudinal sheath and having a central channel as well as a first guiding through-hole, a second end movable from the first end and from the longitudinal sheath and having a second guiding through-hole, and a deformable element fixable to at least the second end. The medical apparatus has a first (retracted) configuration in which the treatment device is extended (Continued)

Figures 1A, 1B, 1C, 1D:
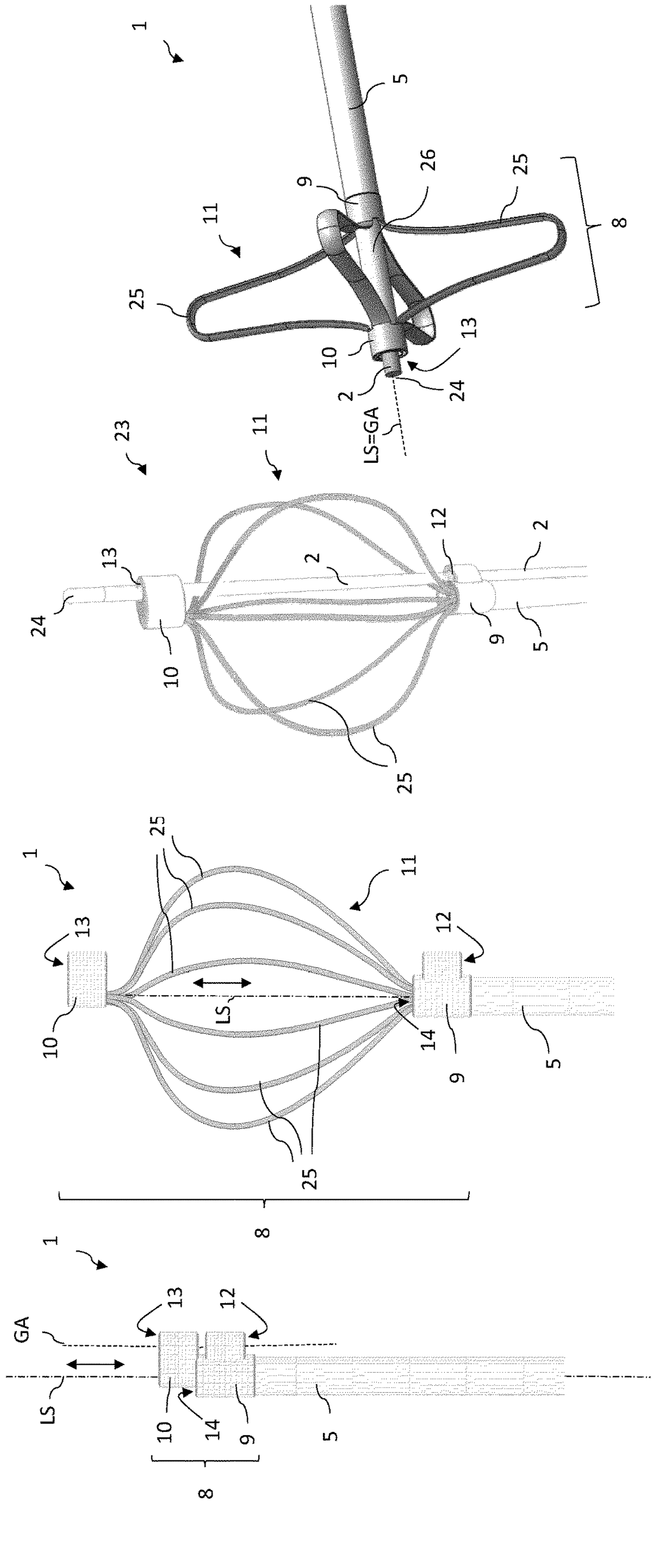

through the first and second guiding through-holes and a second (expanded) configuration in which the treatment device, when inserted into the first guiding through-hole and the second guiding through-hole, is moved towards a central region of the cavity and is maintained in said position during the treatment.

24 Claims, 12 Drawing Sheets

(51) Int. Cl.
*A61B 1/267* (2006.01)
*A61B 1/273* (2006.01)

(56) References Cited

U.S. PATENT DOCUMENTS 6,245,064 B1 * 6/2001 Lesh .......... A61M 25/1002 606/34
6,258,087 B1 * 7/2001 Edwards .......... A61B 18/1206 606/41
6,966,908 B2 * 11/2005 Maguire .......... A61N 7/02 606/41
8,540,704 B2 * 9/2013 Melsky .......... A61B 1/00165 606/2
9,278,019 B2 * 3/2016 Thompson .......... A61F 5/0076
10,779,882 B2 * 9/2020 Long .......... A61B 90/08
12,376,737 B1 * 8/2025 Piskun .......... A61B 1/31
2008/0045842 A1 * 2/2008 Furnish .......... A61B 1/00177 600/478
2008/0275483 A1 * 11/2008 Makower .......... A61B 17/32053 600/114
2014/0296902 A1 10/2014 Huszar et al.
2015/0142041 A1 * 5/2015 Kendale .......... A61B 1/0125 606/190
2017/0027640 A1 2/2017 Kunis et al.
2017/0112569 A1 4/2017 Motosugi et al.
2019/0104933 A1 4/2019 Stern et al.
2019/0282299 A1 9/2019 Fan et al.
2019/0314620 A1 * 10/2019 Chang .......... A61B 5/6852
2023/0079408 A1 * 3/2023 Zhao .......... A61B 1/00082 600/109
2024/0108412 A1 * 4/2024 Yurek .......... A61B 18/26
2025/0160920 A1 * 5/2025 Soden .......... A61B 18/00

OTHER PUBLICATIONS

Office Action dated Mar. 11, 2026, issued in corresponding Indian Patent Application No. 202417037572.

* cited by examiner

ABLATING APPARATUS

The invention relates to a medical apparatus for supporting and centering a treatment device configured to treat the internal walls of a longitudinal cavity, in particular a human cavity. In addition, the invention relates to an ablating and resurfacing system comprising said medical apparatus and a treatment device for the ablation and the resurfacing of the superficial mucosae of a human cavity, in particular the gastro apparatus, more particularly the duodenum. Also, the invention relates to an endoscopic device comprising the medical apparatus or the ablating and resurfacing system.

Type II diabetes is the most prevalent metabolic disease worldwide with a huge impact on the quality life of patient and extremely high cost for the society and the healthcare systems. When adopting a healthier lifestyle does not suffice, Type II diabetes is commonly treated through medications, drugs and surgery.

Obesity is often strictly associated with type II diabetes. It is well known from bariatric surgery clinical studies, that surgeries on the gastrointestinal (GI) tract can contribute to the improvement of insulin resistance and type II diabetes disease extent. Examples of this surgery include gastric and duodenal bypass that present high risk for patients, high cost for caregivers and are not a viable options for non-obese patients or patients in an early stage of the disease.

Several solutions were developed overtime to mimic the effect of bariatric surgery, including:

- physical barriers that prevent the contact between food and duodenal mucosae;
- duodenal mucosae resurfacing (MDR) device based on a balloon inflated with hot liquid; and
- laser devices to target the neural activity in the duodenum.

However, all of them have limitations and side effects. For example, the use of physical barriers can cause nausea, pain, mucosal tear, bleeding, migration and obstruction, with the necessity of device removal overtime. This being therefore not a possible permanent solution. The use of MDR devices can lead to uncontrolled depth of thermal damage to the surface. Also, there is a lack of real time visibility of the portion of tissue actually treated by the surgeon. On the other hand, the employment of laser devices is targeted to the nerve system rather than the mucosae. Also in this case, there is a lack of real time visibility of the portion of tissue actually treated by the surgeon. Furthermore, it is not always possible to ensure an homogeneous delivery of power energy on the tissue to be treated, thereby leading to undesired effects.

WO 2018/033910 describes for example an apparatus for providing feedback to nerve ablation in the wall of the gastrointestinal tract using laser ablation. In particular, the apparatus includes an expandable balloon used for ensuring that the catheter inserted into the duodenum is positioned in the center at the region designed for treatment. Also, the apparatus comprises a laser emitting element to transmit two laser beams for the ablation of the tissue and for detecting the modifications resulting from the impingement of the first laser beam. In order to precisely direct the laser beam, the apparatus finally comprises a deflective optical element coupled with the laser emitting element. Although effective, this apparatus is made of several different components that make it prone to possible malfunction and wear. Also, the laser requires a dedicated optics in order to be correctly directed to the tissue.

Examples of the present disclosure seek to address or at least alleviate the above problems.

According to a first aspect of the invention there is provided a medical apparatus for supporting and centering a treatment device treating the internal walls of a longitudinal cavity, in particular a human cavity, the apparatus comprising:

- a longitudinal sheath insertable in a working channel of an endoscopic device; and
- a positioning element comprising a first end connectable to the longitudinal sheath and having a central channel as well as a first guiding through-hole, a second end configured to be movable from the first end and from the longitudinal sheath and having a second guiding through-hole, and a deformable element fixable to at least the second end;
- wherein in a first configuration, or retracted configuration, the second end of the positioning element is at a first distance from the longitudinal sheath, the first guiding through-hole and the second guiding through-hole being aligned for receiving the treatment device and the deformable element is completely compressed in the direction of the longitudinal sheath, and in a second configuration, or expanded configuration, the second end of the positioning element is spaced apart from the longitudinal sheath at a second distance, wherein the first distance is different from the second distance and the deformable element is radially expanded, thereby touching, at least partially, the internal walls of the cavity so that the first guiding through-hole and the second guiding through-hole are moved away from the internal walls of the cavity and the treatment device, when inserted into the first guiding through-hole and the second guiding through-hole, is moved towards a central region of the cavity and is maintained in said position during the treatment.

In a second aspect of the invention there is provided an ablating and resurfacing system for the ablation and the resurfacing of the superficial mucosae of a human cavity, in particular the gastro apparatus, more particularly the duodenum, the system comprising:

- a medical apparatus according to according to the first aspect of the invention, and a treatment device treating the internal walls of the human cavity,
- wherein in the first configuration of the apparatus, the treatment device is extended through the first guiding through-hole and the second guiding through-hole and in the second configuration of the apparatus, the second end of the positioning element is moved along the treatment device until the deformable element is expanded and the treatment device is moved away from the internal walls of the cavity, in particular towards a central region of the cavity.

In a third aspect of the invention there is provided an endoscopic device having a working channel and comprising an apparatus according to the first aspect of the invention or a system according to the second aspect of the invention, the apparatus or the system being insertable in the working channel of the endoscopic device.

In a fourth aspect of the invention there is provided a method for treating the internal walls of a longitudinal cavity, in particular a human cavity, by means of the apparatus of the first aspect, or of the system according to the second aspect or the endoscopic device of the third aspect.

Other aspects and features are defined in the appended claims.

Examples of the disclosure may make it possible to obtain a reliable apparatus usable for ablation and resurfacing of a tissue in the gastrointestinal region that ensures a correct treatment of the region and a real time visibility of the portion of tissue actually treated by the surgeon.

Examples of the disclosure will now be described by way of example only with reference to the accompanying drawings, in which like references refer to like parts, and in which:

FIGS. 1A-D show the medical apparatus without the treatment device in the first and second configuration and the medial apparatus with the treatment device in the second configuration according to a offset arrangement (1A-C) and according to a coaxial arrangement (1D).

Figure 2B:
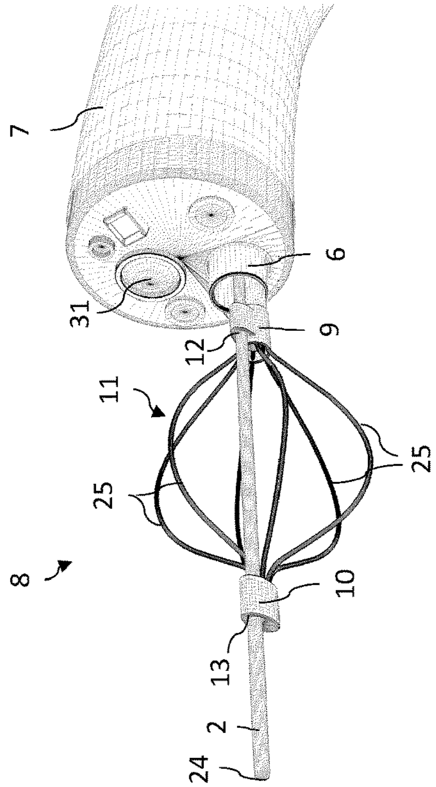
Figure 2C:
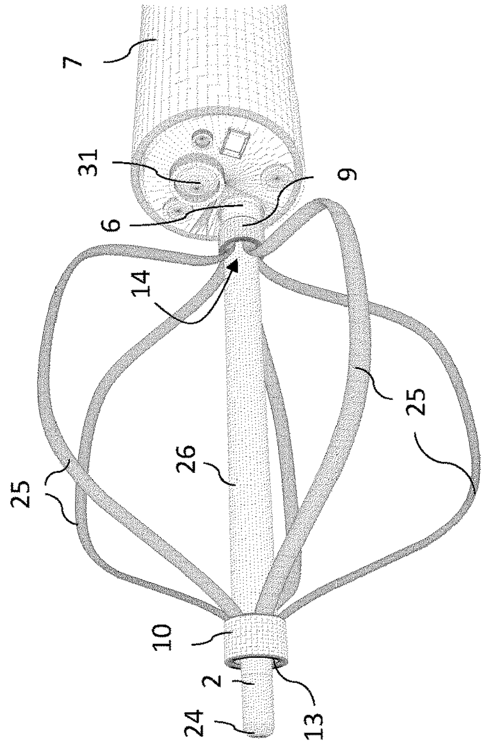
Figure 2A:
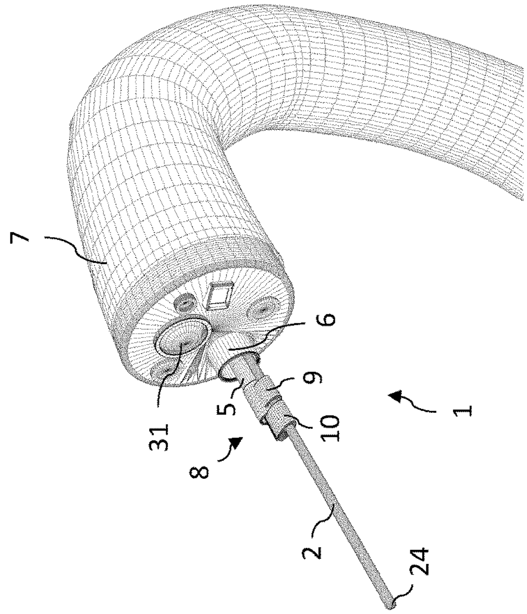
Figure 3D:
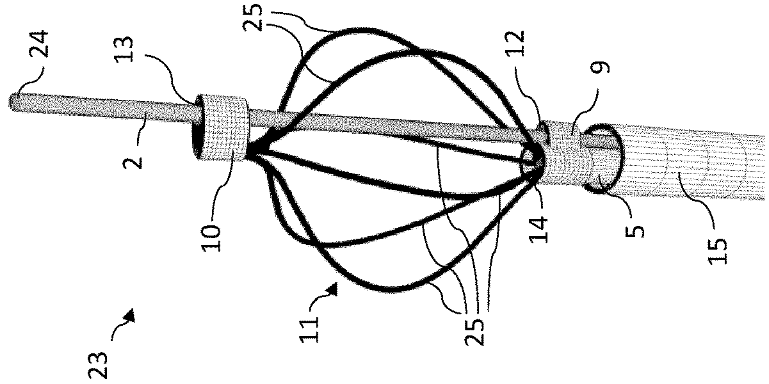
Figure 3C:
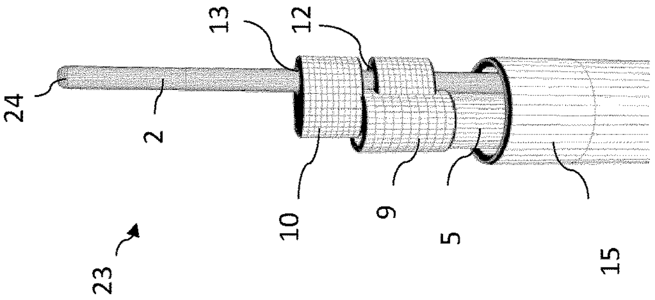
Figure 3B:
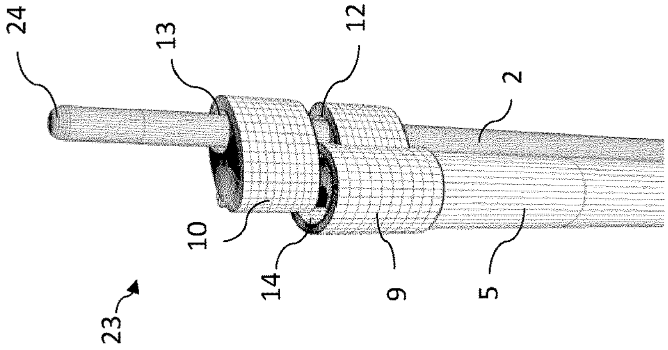
Figure 3A:
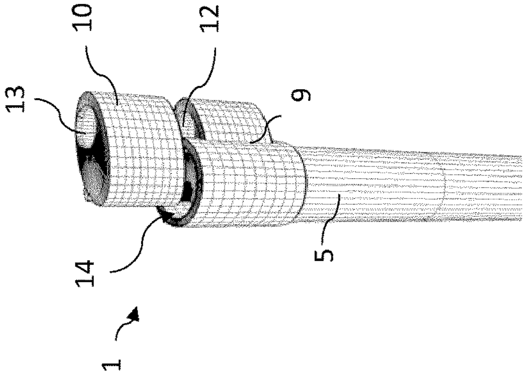

FIGS. 2A-C show the medical apparatus used in an endoscopic device according to an example, wherein the positioning element is in the first and second configuration of the offset arrangement (2A-B), and wherein the positioning element is in the second configuration of the coaxial arrangement (2C).

FIGS. 3A-D show the medical apparatus receiving a treatment device in different steps according to an example of the offset arrangement.

Figure 4B:
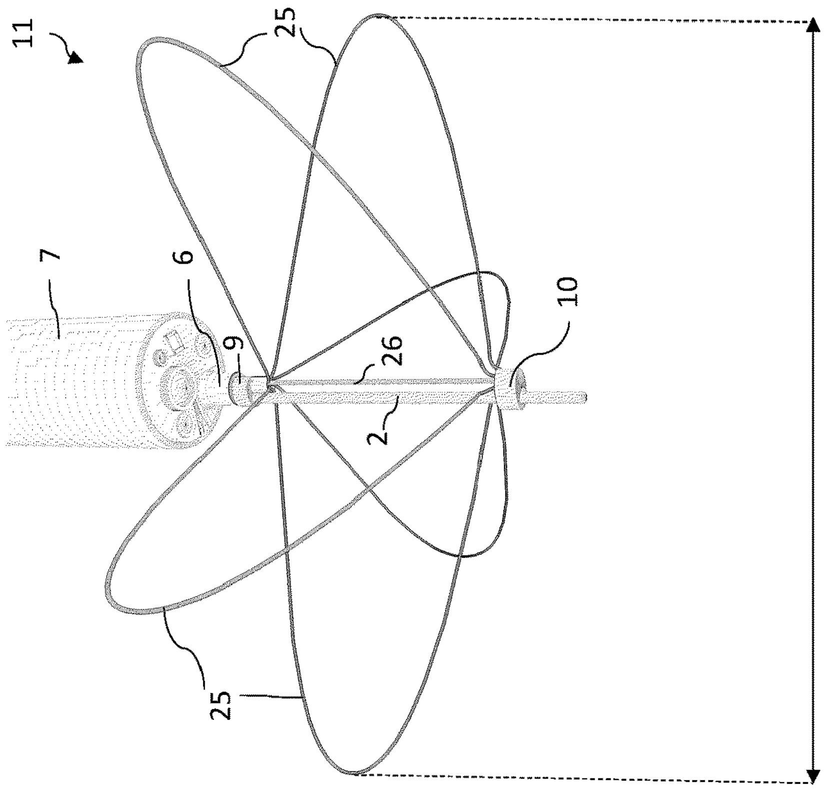
Figure 4A:
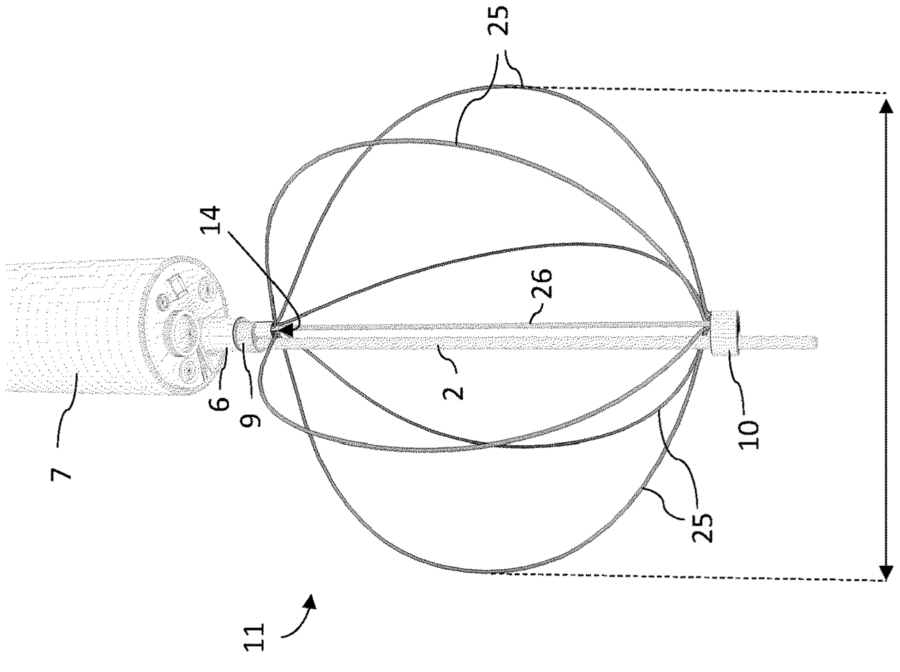

FIGS. 4A-B show the medical device according to another example with the positioning element in the second configuration of the offset arrangement.

FIGS. 5A-G show the functioning of the medical device inserted in a longitudinal cavity of a human body.

Figure 6C:
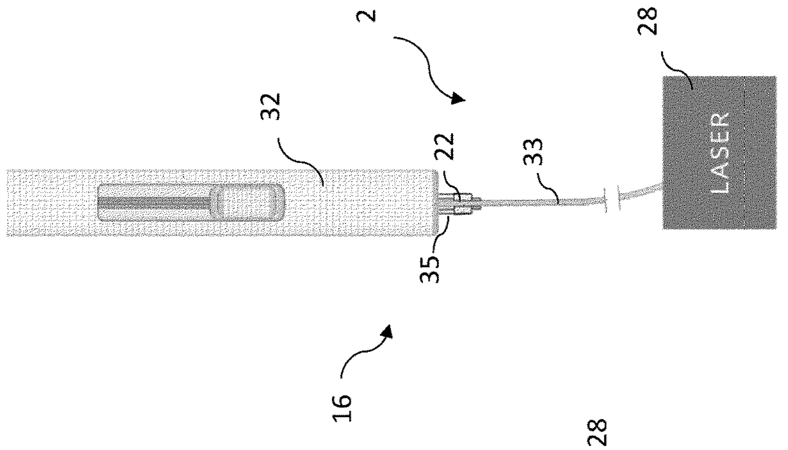
Figure 6B:
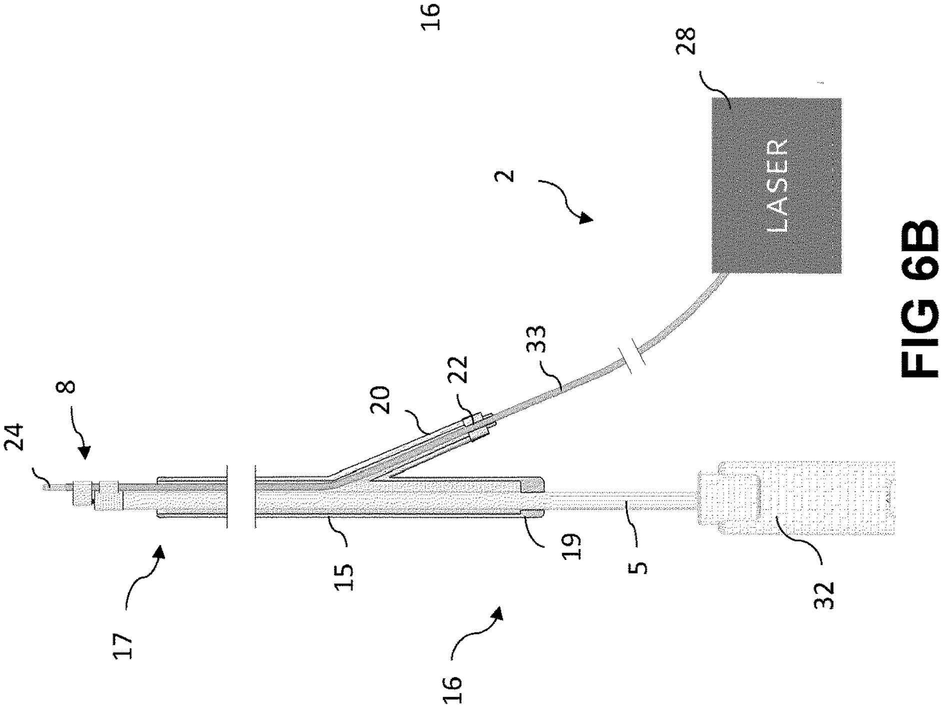
Figure 6A:
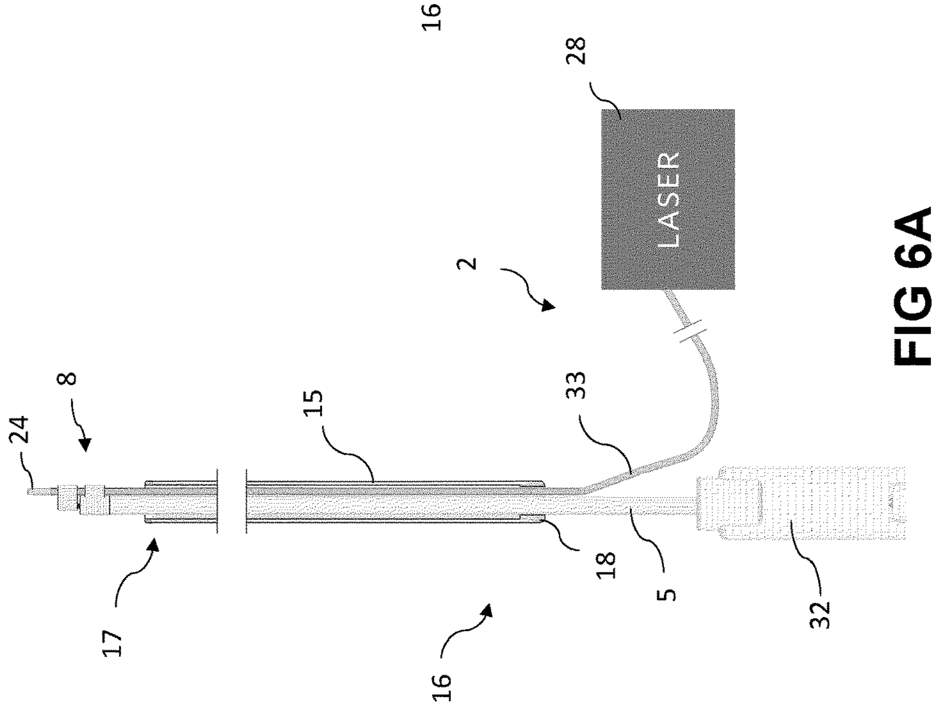

FIGS. 6A-C show detail of connecting ports according to different examples.

Figure 7B:
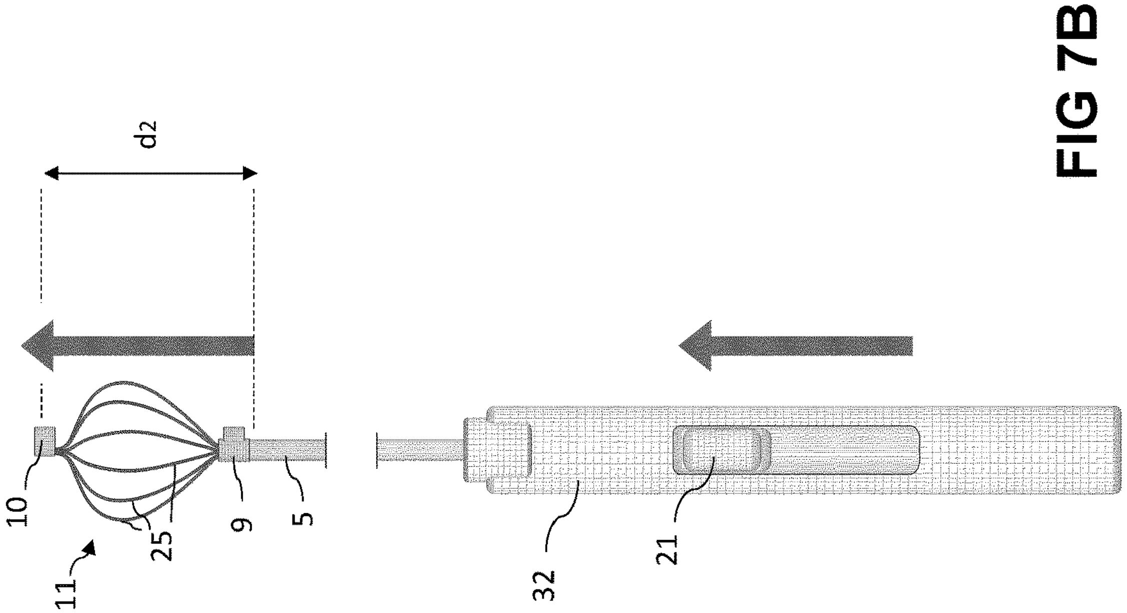
Figure 7A:
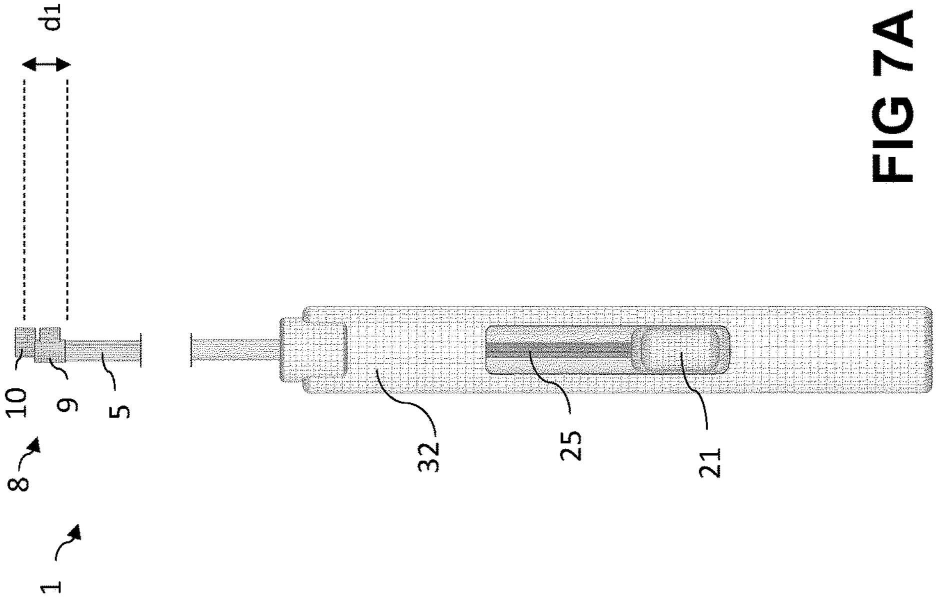

FIGS. 7A-B show the passage from the first configuration to the second configuration of the positioning element according to an example of the offset arrangement.

Figure 8C:
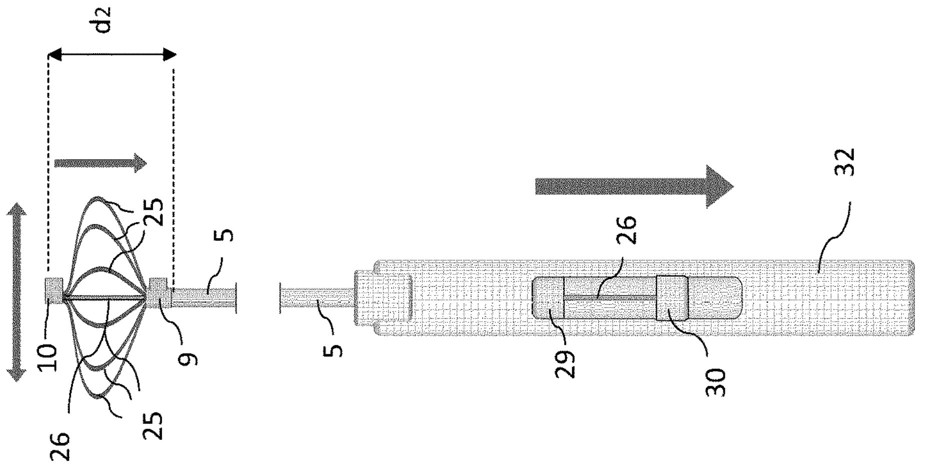
Figure 8B:
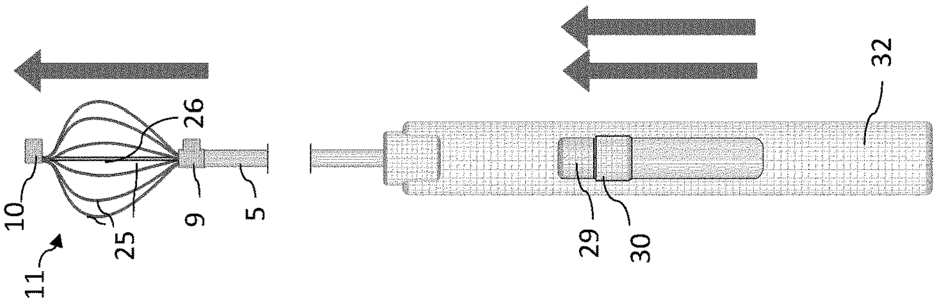
Figure 8A:
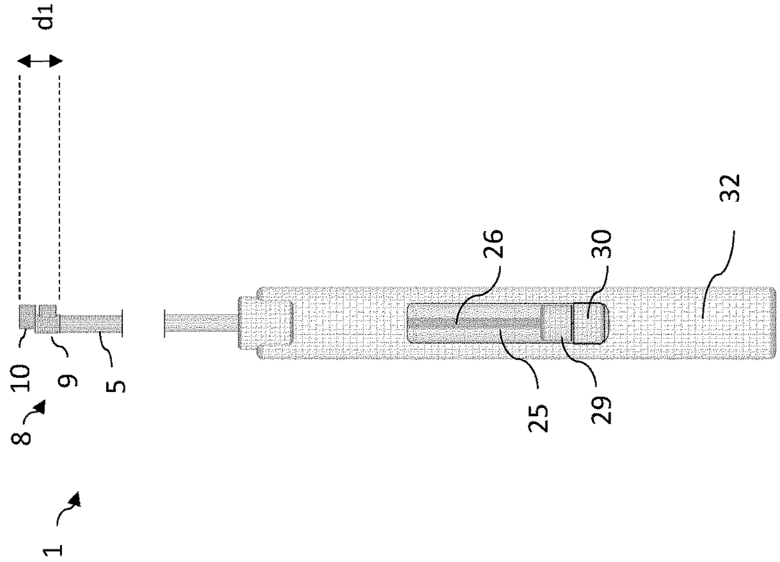

FIGS. 8A-C show the passage from the first configuration to the second configuration of the positioning element according to another example of the offset arrangement.

Figure 9C:
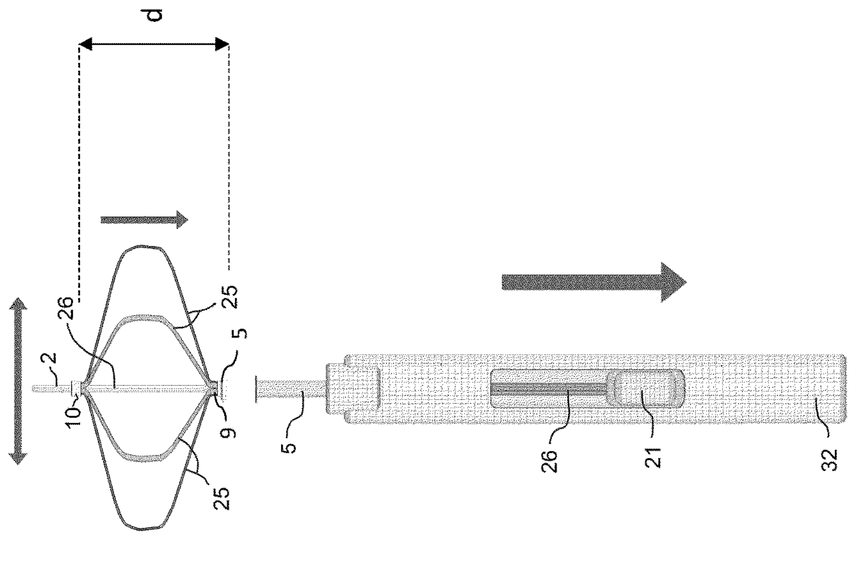
Figure 9B:
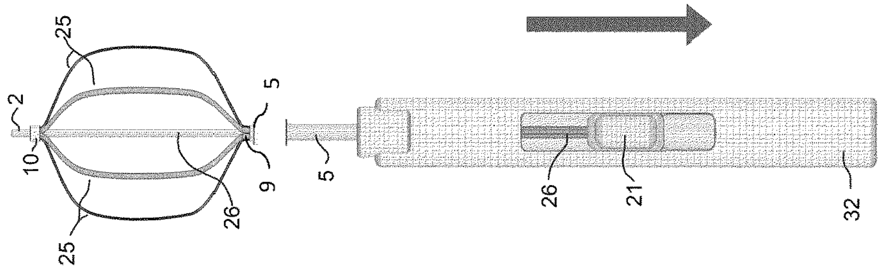
Figure 9A:
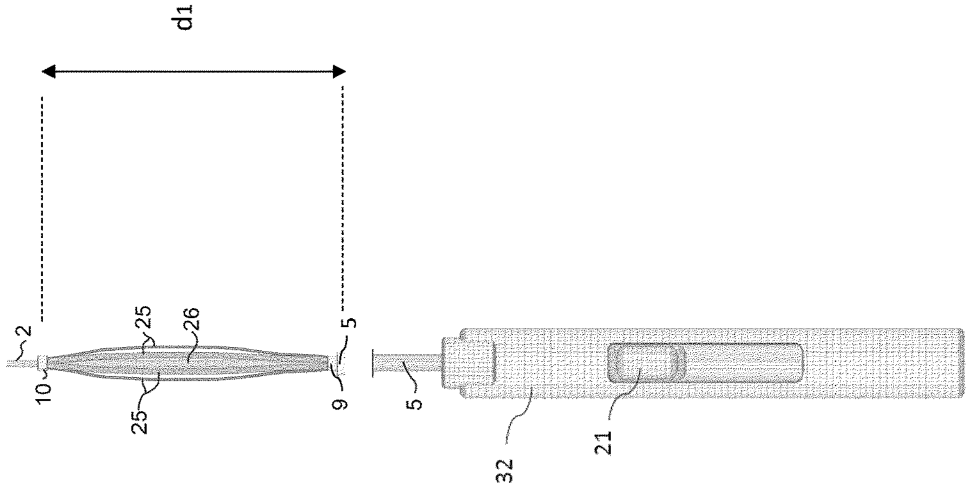

FIGS. 9A-C show the passage from the first configuration to the second configuration of the positioning element according to an example of the coaxial arrangement.

FIGS. 10A-D show the passage from the first configuration to the second configuration of the positioning element according to an additional example of the coaxial arrangement.

Figure 11:
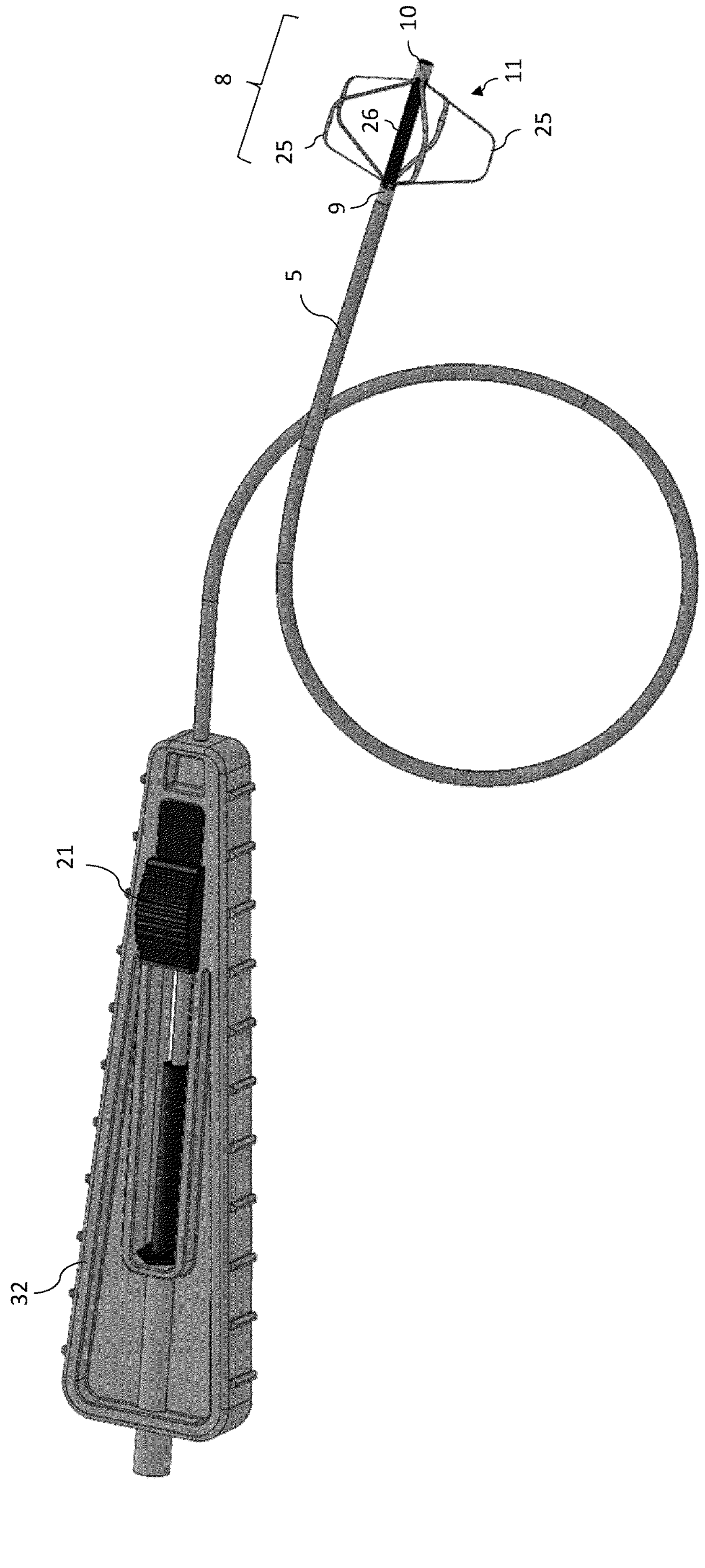
Figure 12A:
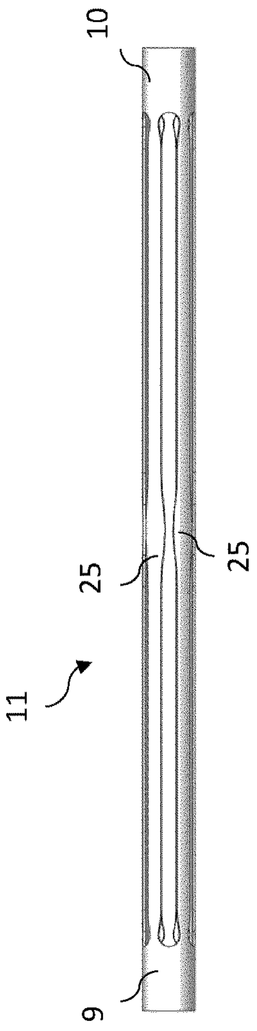
Figure 12B:
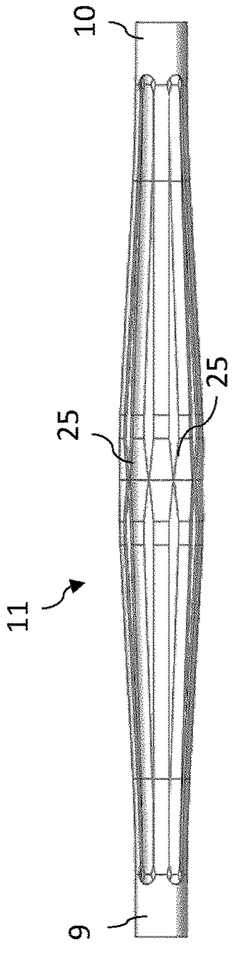
Figure 12C:
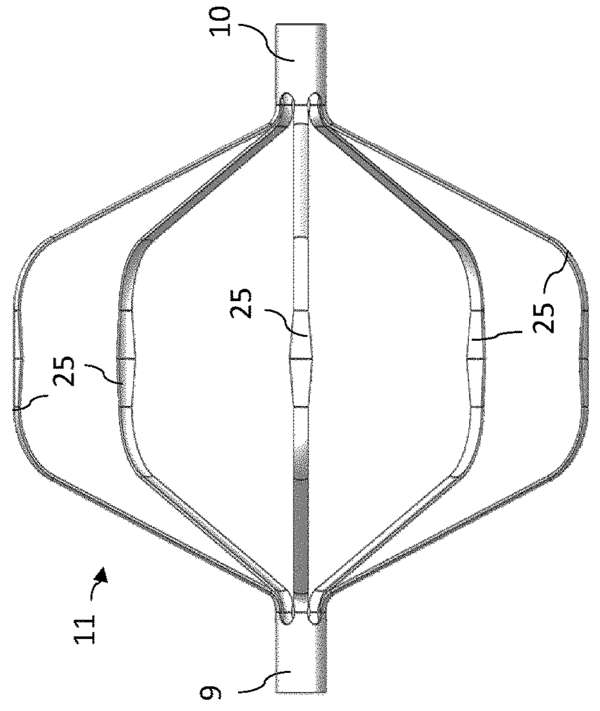

FIG. 11 shows a perspective view of the medical apparatus according to an example of the coaxial arrangement FIGS. 12A-C show different configurations of deformable element according to an example of the coaxial arrangement.

With reference to FIGS. 1A to 1D, the apparatus 1 is suitable for supporting and centering a treatment device 2 treating the internal walls 3 of a human cavity. With treatment device 2 is intended any type of device commonly used for example in the endoscopic procedures that is able to treat the tissue of a human cavity. For example, the treatment can be carried out using light emitting means, thermoelectric means, cutting means, magnetic means, etc. The application of the medical apparatus 1 in the human cavity will be better illustrated in other figures, for example FIGS. 5A-5G.

The apparatus 1 can be set up according to at least two different arrangements, an offset arrangement and a coaxial arrangement, as will be explained in detail below. It is noted that the main difference between the offset arrangement and the coaxial arrangement basically relates to the different position of the treatment device 2 with respect to a central axis of the apparatus 1. Apart this main structural difference, the majority of characteristics and corresponding applications defining the apparatus 1 according to the offset arrangement can also apply to the apparatus 1 according to the coaxial arrangement.

In the offset arrangement (FIG. 1A-1C), the medical apparatus 1 comprises a longitudinal sheath 5 and a positioning element 8 connected to one end of the longitudinal sheath 5. The positioning element 8 comprises a first end 9 that can be connected to the longitudinal sheath 5 and a second end 10. The first end 9 is provided with a central channel 14 and a first guiding through hole 12 located next to, and spaced from, the central channel 14, whereas the second end 10 is provided with a second through-hole 13. According to this example, the central channel 14 is spaced from the first guiding through-hole 12 and the second guiding through-hole 13 is not centered on the second end 10. Therefore, an offset is present between the central channel 14 and the guiding through holes 12, 13.

The second end 10 can be moved from the longitudinal sheath 5 and then from the first end 9 so that the positioning element 8 can assume a first configuration or retracted configuration, as shown in FIG. 1A, and a second configuration or expanded configuration, as shown in FIG. 1B. The movement occurs along the longitudinal axis LS of the longitudinal sheath 5, as shown with the double arrow in the figure. The deformable element 11 of the positioning element 8 is configured to slide through the central channel 14 of the first end 9 so that in the first configuration, the second end 10 of the positioning element 8 is in contact with the first end 9 of the positioning element 8. As will be shown in more detail with reference to FIGS. 7A-B and 8A-C, the distance between second end 10 and the longitudinal sheath 5 varies passing form the first configuration to the second configuration. In particular, in the first configuration this distance (first distance $d_1$) is smaller than in the second configuration (second distance $d_2$) and the deformable element 11 is compressed inside the longitudinal sheath 5. The medical apparatus 1 has therefore an elongated shape like a rod. In this way, it is possible to easily insert the medical device 1 inside a human cavity. As shown in FIG. 1A, in this configuration, the first guiding through-hole 12 and the second guiding through-hole 13 are aligned. The vertical dashed line in the figure shows the presence of a single passage through the two guiding through-holes 12, 13. This is useful for the insertion of a treatment device 2. Advantageously, the treatment device 2 has an elongated shape suitable for passing through this passage. This vertical dashed axis can be denoted as a guiding axis GA and is arranged parallel to the longitudinal axis LS of the longitudinal sheath 5.

In the second configuration, the first end 9 of the positioning element 8 is spaced apart from the second end 10 of the positioning element 8. In particular, the second end 10 is moved forward along the direction of the longitudinal sheath 5, i.e., along the longitudinal axis LS. As shown in FIG. 1B, the positioning element 8 furthermore comprises a deformable element 11 fixable to the second end 10. As mentioned above, the deformable element 11 is configured to slide through the central channel 14 of the first end 9. It is noted that in the first configuration the deformable element 11 is completely compressed inside at least the longitudinal sheath 5, and in a second configuration the deformable element 11 is radially expanded. In other words, moving the second end 10 away from the first end 9 causes the deformable element 11 to be extracted from the longitudinal sheath 5 through the central channel 14 and to be expanded.

According to an example (e.g. FIG. 1B), the deformable element 11 comprises a plurality of deformable threads 25. Each thread 25 can extend from the second end 10 to the first end 9. It is noted that the threads 25 are fixed at the second end 10 but are not fixed to the first end 9 of the positioning element 8. As a matter of fact, the threads 25 can be configured to pass through the central channel 14 and can be fixed at an internal portion of the longitudinal sheath 5 (not shown in the figure). In an example, the plurality of deformable threads 25 are made of a material having shape memory and superelasticity, in particular of a metal alloy of nickel and titanium (i.e. Nitinol). Of course, the deformable element 11 can be made of different materials that are suitable for the purpose of the present disclosure.

The first and second guiding through-holes 12, 13 are configured for receiving a treatment device 2. Advantageously, the treatment device 2 is inserted in the guiding through-holes 12, 13 when the positioning element 8 is in the first configuration, as will be explained in detail in FIGS. 3A-3D. FIG. 1C shows on the other hand, the situation wherein the treatment device 2 is inserted into the two guiding through-holes 12, 13 and the positioning element 8 is in the second expanded configuration. The combination of the medical apparatus 1 with the treatment device 2 can be defined as an ablating and resurfacing system 23. As will be explained in more detail with the following figures, in the second configuration of the apparatus 1, the second end 10 of the positioning element 8 is moved along the treatment device 2 until the deformable element 11 is expanded. In this way, the first and second guiding through-holes 12, 13, and consequently the treatment device 2, are moved away from the internal walls 3 of the human cavity 4, in particular towards a central region of the human cavity 4.

In an alternative example, the first guiding through-hole 12 is coaxial with the central channel 14 and the second guiding through-hole 13 is centered on the second end 10 (coaxial configuration). This is shown for example in FIG. 1D. In this case, according to the coaxial arrangement, the guiding axis GA coincides with the longitudinal axis LS of the longitudinal sheath 5 and the treatment device 2 can slide along the longitudinal axis LS of the longitudinal sheath 5. It is noted that the deformable element 11 is fixable also to the first end 9 of the positioning element 8 so that that in the first configuration the second end 10 of the positioning element 8 is moved away from the first end 9 of the positioning element 8 so that that the first distance $d_1$ is greater than the second distance $d_2$ and the deformable element 11 is compressed outside the longitudinal sheath 5. FIG. 1D only shows the deformable element 11 in the second or expanded configuration. The first or retracted configuration for this coaxial arrangement is illustrated in FIGS. 9A-9C and 10A-10D.

It is noted that similarly to offset arrangement, the deformable element 11 in the coaxial arrangement can comprise a plurality of deformable threads 25. Each thread 25 can extend from the second end 10 to the first end 9. It is noted that the threads 25 are fixed to both the first end 9 and to the second end 10 of the positioning element 8. As mentioned above, the plurality of deformable threads 25 can be made of a material having shape memory and superelasticity, in particular of a metal alloy of nickel and titanium. Of course, the deformable element 11 can be made of different materials that are suitable for the purpose of the present disclosure.

In examples for both the offset and coaxial arrangement, in the second configuration, the deformable element 11 can assume a basket-shaped structure. Of course, the deformable element 11 can be configured in several different ways. For example, the deformable element 11 can comprise one or more components able to vary their shape from a contracted to an extended configuration after the supply of a fluid (gas or liquid). The deformable element 11 can have the shape of a balloon. In case of the presence of a distance varying element 26, the deformable element 11 can be changed from an almost round shape to a more compressed, flattened shape. The presence of a distance varying element 26 will be described for example with reference to FIGS. 4A-4B.

FIGS. 2A, 2B and 2C illustrate the application of the medical apparatus 1 in an endoscopic device 7. The endoscopic device 7 has at least a working channel 6 into which the medical apparatus 1, or the system 23, is inserted. The device 7 can be an endoscope for gastroscopy, in particular a flexible endoscope. In particular, FIGS. 2A and 2B illustrate the application of the medical apparatus 1 of FIGS. 1A-1C, i.e. in the offset arrangement, whereas FIG. 2C illustrates the application of the medical apparatus 1 of FIG. 1D, i.e. in the coaxial arrangement.

In FIG. 2A the positioning element 8 of the medical apparatus 1 is in the retracted configuration. As a matter of fact, the first end 9 is in contact with the second end 10 of the positioning element 8 and the medical apparatus 1 can be easily moved through the working channel 6. On the other hand, in FIG. 2B, the positioning element 8 of the medical apparatus 1 is in the expanded configuration. As a matter of fact, the second end 10 is spaced apart from the first end 9 and the deformable threads 25 of the deformable element 11 are expanded forming a basked-shaped structure. The endoscopic device 7 can be inserted in a human cavity (e.g. duodenum) when the positioning element 8 is in the first configuration. When it is found the tract of the human cavity to be treated, the positioning element 8 can be moved to the second configuration so that the deformable thread can touch the internal walls of the cavity and can cause the movement of the treatment device 2 from a region of the cavity close to the internal walls towards the central region of the cavity. It is noted that the deformable element 11 in the extended configuration can also serve to maintain the treatment device 2 in position during the treatment, when required.

The endoscopic device 7 can have all the features typical of a conventional device used in endoscopic surgery. For example, the device 7 can comprise a camera 31 for monitoring the effect of the treatment device 2 on the internal walls 3 of the cavity 4. The monitoring can be carried out on real-time basis.

In one example, the treatment device 2 is a laser system, in particular emitting a radiation having a wavelength comprised between 1900 nm and 2100 nm or between 10200 nm and 10600 nm. For example, the treatment device 2 can be a laser optical fiber, in particular a thulium fiber laser. This type of laser serves to ablate the surface of the target tissue conserving the surrounding tissue thanks to the superficial precise action of this specific wavelength. The photo-thermal effects indeed increase the temperature of the water contained on the tissue causing the ablation or denaturation of the tissue without deep propagation of the thermal effect on the surrounding tissues. With laser optical fiber is intended here a laser generator for generating a laser radiation coupled to an optical fiber for conducting the laser radiation through the human cavity, only the optical fiber being inserted into the cavity. Advantageously, the optical fiber can comprise one or more emitting points, usually on the tip, for emitting the laser radiation.

In another example, the treatment device 2 can be an optical fiber laser system comprising a laser generator 28 coupled to an optical fiber structure 33 having a tip portion 24 for a diffusive or radial laser emission.

FIG. 2C shows the positioning element 8 in the expanded configuration of an alternative medical apparatus 1 in the coaxial arrangement. In particular, the medical apparatus 1 of FIG. 2C has the same characteristics of the apparatus 1 of FIG. 2B with the difference that the treatment device 2 is not offset with respect to the central channel 14 but is coaxial with this channel.

FIGS. 3A-3D illustrate the medical apparatus 1 and the ablating system 23 according to two examples of the offset arrangement. In a first example (FIGS. 3A-3B) the apparatus 1 and the system 23 correspond to the apparatus and system already described in FIGS. 1A-C. In a second example (FIGS. 3C-3D), the apparatus 1 and the system 23 further comprise an external sheath 15 containing both the longitudinal sheath 5 and the treatment device 2. The external sheath 15 can be inserted in the working channel 6 of the endoscopic device 7. Since the external sheath 15 contains both the medical apparatus 1 and the treatment device 2, the sheath 15 is useful to facilitate the insertion in the working channel 6 of the endoscopic device 7.

FIGS. 4A and 4B illustrates the medical apparatus 1 according to another example of the offset arrangement. The medical apparatus 1 can furthermore comprise a distance varying element 26 extending between the first end 9 and the second end 10 of the positioning element 8 and fixable to the second end 10 for reducing or increasing the distance between said first end 9 and said second end 10 when the positioning element 8 passes from the first configuration to the second configuration and vice versa, the deformable element 11 surrounding (at least in part) the distance varying element 26.

In particular, as shown in FIGS. 4A-4B, the distance varying element 26 can be a wire-shaped element extending longitudinally from the first end 9 to the second end 10 and being slidably movable inside at least the longitudinal sheath 5, for example passing through the central channel 14 of the first end 9.

The distance varying element 26 can be actuated when the deformable element 11 is in the extended configuration (FIG. 4A). In this configuration, the deformable threads 25 are symmetrically arranged around the treatment device 2 thereby forming a basket structure. The maximum width of this basket structure is denoted with the letter W in the figure. If the human cavity 4 inside which the medial apparatus 1 is inserted has the same or a smaller width, the deformable threads 25 would be in contact with the internal walls 3 of such a cavity 4. However, in case the cavity with is greater than the value of the maximum width W, the extended threads 25 would not be able to touch the internal walls 3 and the treatment device 2 would not be moved toward the central region of the cavity. To overcome this problem, the distance varying element 26 can be actuated. In this case, the distance between the first and second ends 9, 10 is reduced so that the deformable threads 15 can be further expanded due to compression and can get in close contact with the internal walls 3 of the body lumen being treated. As shown in FIG. 4B, the maximum width W is increased to a greater value denoted as W* in the figure.

FIGS. 5A-5G illustrate a possible approach to insert the medical apparatus 1 with the treatment device 2 in the human cavity 4. In this example, the cavity 4 is the duodenum area and the successive opening steps of the deformable element 11 are illustrated. Thanks to the operation of the medical apparatus 1, the treatment device 2, in this case an optical fiber laser, can be easily moved in the middle of the cavity 4. When the treatment device 2, i.e., the optical fiber laser, is well positioned in the center of the cavity 4, the laser can be activated in order to deliver the laser radiation to the internal surfaces 3 of the cavity 4. The central position of the treatment device 2 and the radial emission 27 guarantees the homogeneous distribution on the target surface. The quantity of energy applied depends on the power laser output, the geometry of the cavity and the desired effect on the target tissue.

Figures 5A, 5B, 5C, 5D, 5E, 5F, 5G:
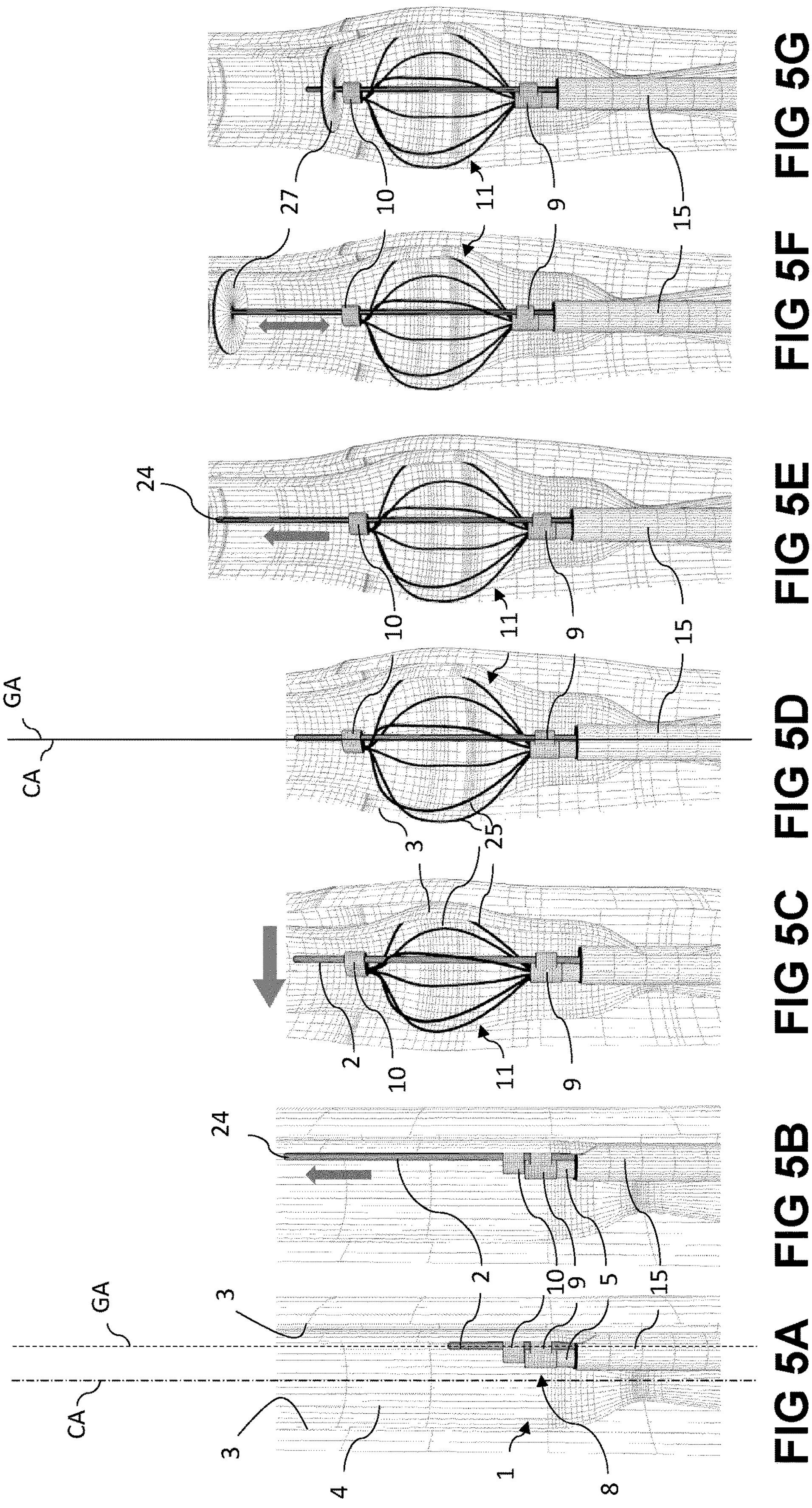

According to FIG. 5A, a user, for example a surgeon, inserts the medical apparatus 1 combined with the treatment device 2 in the human cavity 4 and reaches the tract of the human cavity 4 needed to be treated. According to an example, the medical apparatus 1 has a longitudinal guiding axis GA. The guiding axis GA is an imaginary axis passing through the first and second guiding through-holes 12, 13 of the first and second ends 9, 10, respectively (as also shown in FIG. 1A). When the medical apparatus 1 is inserted in the cavity 4, the apparatus 1 is usually not centered in the cavity 4. As a matter of fact, the longitudinal guiding axis GA is shifted from a cavity central axis CA, in particular to the right according to the example of FIG. 5A. The central axis CA is an imaginary axis passing in the middle of the longitudinal cavity 4 and being almost equidistant from the internal walls 3 of said cavity 4. In FIG. 5B, the treatment device 2, i.e., the optical fiber laser, is extracted on the cavity 4. In this way, the tip 24 of the device 2 is moved away from the positioning element 8 and therefore from the longitudinal sheath 5. In FIG. 5C, the user can set the medical apparatus 1, and therefore the positioning element 8, in the second configuration. In this way, the deformable element 11 is expanded and the deformable threads 25 touch the internal walls 3 of the cavity 4, thereby moving, or rather pushing, the medical apparatus 1 with the treatment device 2 to the left towards the cavity central axis CA (see the horizontal arrow in the figure). In other words, according to an example, the passage from the first configuration to the second configuration causes a variation of the distance between the longitudinal guiding axis GA and the external walls 3 of the cavity 4. In FIG. 5D, the treatment device 2 is positioned in the middle of the cavity 4. As a matter of fact, the longitudinal guiding axis GA almost corresponds to the central axis CA. In FIG. 5E, the tip 24 of the treatment device 2 is further moved forward and is positioned on the correct longitudinal position following the user purpose. This procedure can be carried out using the camera 31 of the endoscopic device 7. In FIG. 5F, the treatment device 2, for example the laser system, is activated and the treatment device 2 delivers a laser radiation 27 by the radial/diffusive tip 27. In FIG. 5G, the treatment device 2 can be moved backwards simultaneously emitting the laser radiation 27 and delivering the energy on the cavity surface. In particular, according to an example, the treatment device 2 extends longitudinally and is configured to slide along the direction of the longitudinal sheath 5 through the first guiding through-hole 12 and the second guiding through-hole 13 when the apparatus 1 (e.g. the positioning element 8) is in the first configuration as well as in the second configuration.

The position in the middle of the cavity 4 of the treatment device 2 allows to have on the target tissue the same treatment, i.e., laser divergence and the same laser intensity causing the same desired effect. Without the correct position of the tip 24 the surfaces of the cavity 4 will be invested by different energy concentrations having non-homogeneous ablation effects. Different laser intensities are at the origin of non-homogeneous effects that could be introduce undesired effects. In this asymmetric configuration the laser effect could be too ablative on the closest areas to the tip 24 and too low effects on the areas far from the tip 24.

FIGS. 5A-5G illustrate the application of the apparatus 1 and in particular an auto-centering function of the apparatus 1 according to the offset arrangement. It is however noted that the same auto-centering function also applies to the apparatus 1 according to the coaxial arrangement. Accordingly, the steps described with reference to FIG. 5A-5G will not be repeated for the apparatus 1 according to the coaxial arrangement.

In applying such a technique with current flexible endoscopes, the medical apparatus 1 and treatment device 2 go through the same working channel 6, typically 3.7-4.2 mm diameter. The medical apparatus 1 and treatment device 2 inside to the external sheath 15, having a diameter of 2-3 mm, are well supported on the working channel lumen 6. The working channel of a flexible endoscope is commonly centrally located along the endoscope body. A typical endoscope has its tip and the segment at the distal end of its shaft to be able to deflect in two opposite directions. The external sheath 15 with inside the medical apparatus 1 and treatment device 2 has a good flexibility without interference with the movements of the endoscopic device 7. When the external sheath 15 goes through the working channel 6 of the endoscopic device 7, the medical apparatus 1 and treatment device 2 do not interfere with each other when the surgeon manipulates them independent from each other. When the medical apparatus 1 and treatment device 2 go through the external sheath 15 these two instruments do not interfere with each other also thanks to the external jacket (typically Tetzel) of the surface of the optical fiber structure 33. Thus, the medical apparatus 1 and treatment device 2 can be manipulated free from mutual interference.

In examples, the ablating system 23 comprises a control unit for controlling the energy output of the treatment device 2 in case the treatment device 2 is a laser system. In addition or in alternative, the control unit serves for controlling the movement of the treatment device 2 through the first guiding through-hole 12 and the second guiding through-hole 13. In addition or in alternative, the control unit serves for controlling the movement of the treatment device 2 through the first guiding through-hole 12 and the second guiding through-hole 13 based on the energy output of the treatment device 2 in case the treatment device 2 is a laser system. Advantageously, to activate the control system a footswitch may be used by the user to start and stop the laser emission of a laser system connected to an optical fiber.

In an example, the external sheath 15 comprises a proximal inserting end 16 and a distal end 17. This is shown in FIGS. 6A and 6B. Although these figures only illustrate the apparatus 1 according to the offset arrangement, the same characteristics also apply to the apparatus 1 according to the coaxial arrangement.

As shown in FIG. 6A, the proximal inserting end 16 can comprise a single port 18 for the passage of the longitudinal sheath 5 and of the treatment device 2. The treatment device 2 can comprise a laser generator 28 for the generation of the laser radiation passing through an optical fiber structure 33 coupled to the laser generator 28.

Alternatively, as shown in FIG. 6B, the proximal inserting end 16 can comprise a first port 19 for the passage of the longitudinal sheath 5 and a second port 20 for the passage of the treatment device 2. Also in this case, the treatment device 2 can comprise a laser generator 28 for the generation of the laser radiation passing through an optical fiber structure 33 coupled to the laser generator 28.

In both configurations of FIGS. 6A and 6B, an end of the longitudinal sheath 5 is connected to an end piece element 32 that can be maneuvered by a user.

In addition, the proximal inserting end 16 can comprise at least a luer-lock element 22 for maintaining in position the element passing through the proximal inserting end 16. For example, the luer-lock element 22 can fix the position of the optical fiber of the treatment device 2. During the insertion and retraction of the optical fiber, this element is unlocked.

Advantageously, the external sheath 15 can be made of a deformable material.

FIG. 6C illustrates a connection configuration according to another example. Whereas FIGS. 6A and 6B show a configuration wherein the ports 18, 19 and 20 are located at one end of the hand piece element 32, i.e. between the hand piece element 32 and the tip 24, FIG. 6C shows a configuration where a single port 35 is located on the opposite side of the hand piece element 32. The configurations of FIGS. 6A-6B are suitable for an offset arrangement and the configuration of FIG. 6C is suitable for a coaxial arrangement.

FIGS. 7A and 7B illustrate the passage from the first configuration to the second configuration of the positioning element 8 according to an example of the offset arrangement. The apparatus 1 further comprises an actuating element 21 for causing the passage from the first configuration to the second configuration and vice versa, wherein in particular one end of the deformable element 11 is connectable to said actuating element 21, the actuating element 21 being configured to slide along the direction of the longitudinal sheath 5. Using the hand piece element 32 by the movement of the actuating element or knob 21, the user can move the deformable threads 25 from the collapsed position (FIG. 7A) inside to the longitudinal sheath 5 to the open position (FIG. 7B) with the deformable threads 25 expanded outside to the sheath 5. Moving the knob 21 in the opposite side the user can compress the deformable threads 25 inside to the sheath 5. It is noted that the deformable threads 25 are connected to the actuating element 21. In other words, the deformable threads 25 connect the actuating element 21 to the second end 10 of the positioning element 8.

These figures describe a first distance $d_1$ and a second distance $d_2$, wherein the first distance $d_1$ represents the distance between the second end 10 and the longitudinal sheath 5, in particular an extremity of the longitudinal sheath 5 in the first (retracted) configuration, and the second distance $d_2$ represents the distance between the second end 10 and the longitudinal sheath 5, in particular an extremity of the longitudinal sheath 5 in the second (expanded) configuration. It is noted that the passage from the first configuration (FIG. 7A) to the second configuration (FIG. 7B) determines an increase of the distance between the second end 10 and the longitudinal sheath 5, i.e. $d_1 < d_2$.

FIGS. 8A-8C illustrate the similar concept of FIGS. 7A-7B according to another example, in particular according to the example wherein a distance varying element 26 is present. Differently from the configuration of FIGS. 7A-7B, the actuating element comprises an upper actuating element 29 connected to the deformable threads 25 and a lower actuating element 30 connected to the distance varying element 26. Advantageously, the lower actuating element 30 allows the passage of the deformable threads 25, for example via a through-hole. Using the hand piece element 32 by the movement of both the upper and lower actuating elements 29, 30, the user can move the deformable threads 25 from the collapsed position (FIG. 8A) inside to the longitudinal sheath 5 to the open position (FIG. 8B) with the deformable threads 25 expanded outside to the sheath 5. Moving the lower actuating element 30 in the opposite side, the user can reduce the distance between the first end 9 and second end 10 of the positioning element 8, thereby increasing the width of the deformable element 11. Moving further moving the upper actuating element 29 backwards, the deformable threads 25 can be compressed inside to the sheath 5.

It is noted that the deformable threads 25 are connected to the upper actuating element 29 and the distance varying element 26 is connected to the lower actuating element 30. In other words, the deformable threads 25 connect the second end 10 of the positioning element 8 to the upper actuating element 29, whereas the distance varying element 26 connects the second end 10 of the positioning element 8 to the lower actuating element 30.

Also in this case, by passing from the first configuration (FIG. 8A) to the second configuration (FIG. 8C) the distance between the second end 10 and the longitudinal sheath 5 increases, i.e. $d_1 < d_2$.

In the coaxial arrangement, the distance varying element 26 can be a tube-shaped element extending longitudinally from the first end 9 to the second end 10 and being slidably movable inside at least the longitudinal sheath 5 and configured to receive the treatment device 2, the first guiding through-hole 12 and the second guiding through-hole 13 being part of the distance varying element 26. In other words, the first guiding through-hole 12 can correspond to the hole of the (tube-shaped) distance varying element 26 at the first end 9 of the positioning element 8. The second guiding through-hole 13 can correspond to the hole of the (tube-shaped) distance varying element 26 at the second end 10 of the positioning element 8. This is shown for example in FIGS. 1D and 2C, in the coaxial arrangement, wherein the guiding axis GA coincides with the longitudinal axis LS of the longitudinal sheath 5.

FIGS. 9A-9C and FIGS. 10A-10D illustrate the passage from the first (retracted) configuration to the second (expanded) configuration in the coaxial arrangement. It is noted that the passages described for the apparatus 1 according to the offset arrangement (FIGS. 7A-B and 8A-C) also apply to the apparatus 1 according to the coaxial arrangement. Therefore, same steps and structural elements are not repeated here. As shown in FIG. 9A, in the first configuration the deformable element 11 has a retracted shape and extends longitudinally in the direction of the longitudinal sheath 5. In this case, the apparatus 1 can easily be inserted into the human cavity. By acting on the actuating element 21, the second end 10 is moved (pulled) towards the longitudinal sheath 5, i.e. the first end 9. Accordingly, the deformable elements 11 takes an expanded shape. It is noted that by passing from the first configuration (FIG. 9A) to the second configuration (FIG. 9C) the distance between the second end 10 and the longitudinal sheath 5 decreases, i.e. $d_1 > d_2$.

Figure 10D:
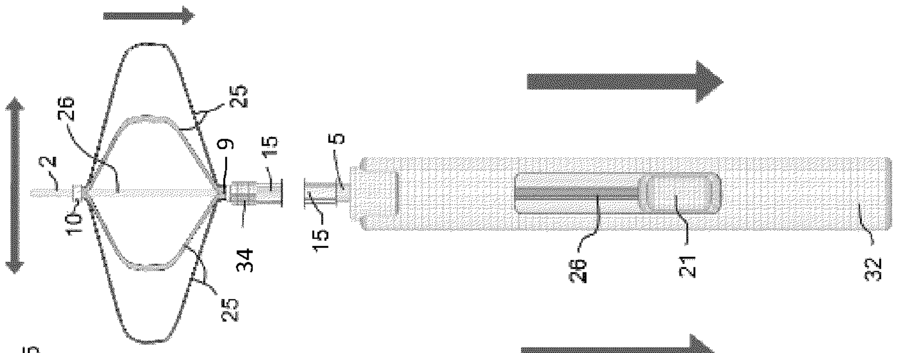
Figure 10C:
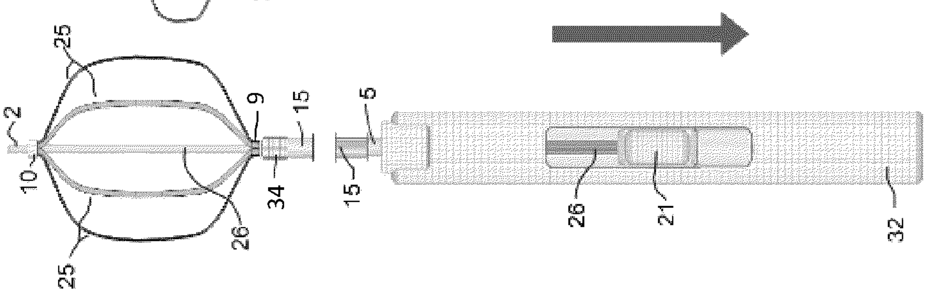
Figure 10B:
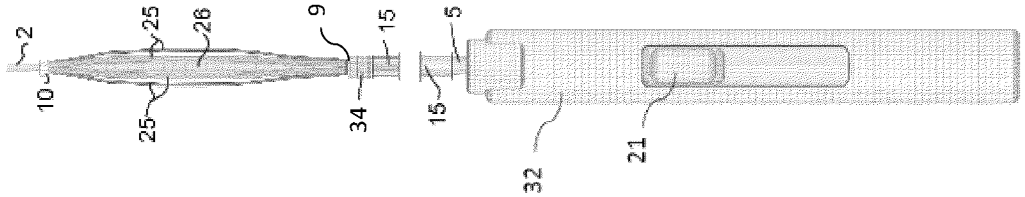
Figure 10A:
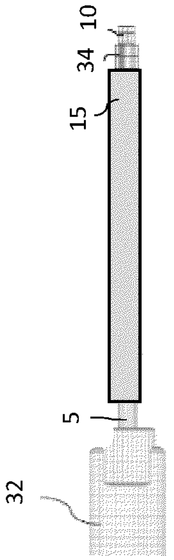

FIGS. 10A-10D describe the same procedure as in FIGS. 9A-9C. The only difference here is that the apparatus 1 comprises an external sheath 15 surrounding the deformable element 11 for protection purposes (FIG. 10A). The deformable element 11 can be pushed out form the external sheath 15 at an external sheath extremity 34, wherein the deformable element 11 maintains its retracted shape (FIG. 10B). By acting on the actuating element 21, the second end 10 is moved (pulled) towards the longitudinal sheath 5, i.e. the first end 9. Accordingly, the deformable elements 11 takes an expanded shape. It is noted that by passing from the first configuration (FIG. 10B) to the second configuration (FIG. 10D) the distance between the second end 10 and the longitudinal sheath 5 decreases, i.e. $d_1 > d_2$ (not shown in the figure but similar to FIGS. 9A-9C).

FIG. 11 describes a possible example of an apparatus 1 according to the coaxial arrangement, wherein an end of the longitudinal sheath 5 is connected to an end piece element 32 that can be maneuvered by a user by the actuating element 21.

FIGS. 12A-C illustrate the shape variation of the deformable element 11 used in an apparatus 1 according to the coaxial configuration. In FIG. 12A, the deformable element 11 has an elongated shape, wherein the threads 25 are all parallel to each other without a specific shape. For example, the deformable element 11 can have this shape when located inside the external sheath 15 (FIG. 10A). In FIG. 12B, the deformable element 11 has always an elongated shape, but the threads 25 are slightly deformed (pre-shaped). For example, the deformable element 11 can have this shape when extracted from the external sheath 15 (FIG. 10B) or in the initial situation of FIG. 9A. In FIG. 12C, the deformable element 11 is expanded and can have the shape of a basket. For example, the deformable element 11 can have this shape in the second configuration (FIG. 9C, 10D). Between the pre-shape form and the expanded form, the deformable element 11 can assume intermediates shapes, such as for example in FIGS. 8B, 9B, and 10C.

The apparatus 1—both according to the offset arrangement and the coaxial arrangement—can be used for a method for treating the internal walls of a longitudinal cavity, in particular a human cavity.

In particular, the method can be used for treating a human cavity in the gastro intestinal apparatus, with the purpose of targeting diseases of such apparatus, including Barrett's esophagus and other diseases and cancers formations. In addition or alternative, the method can be used for treating human cavities in the gastro intestinal apparatus, with the purpose of targeting metabolic diseases, in particular diabetes, nash, or fatty liver disease, and food intolerances.

The method can furthermore be used for treating a human cavity in the respiratory system, with the purpose of targeting respiratory diseases.

The method can also be used for treating a human cavity in the cardiac system, with the purpose of targeting cardiac diseases.

Although a variety of techniques and examples of such techniques have been described herein, these are provided by way of example only and many variations and modifications on such examples will be apparent to the skilled person and fall within the spirit and scope of the present invention, which is defined by the appended claims and their equivalents.

The invention claimed is:

1. A medical apparatus for supporting and centering a treatment device for treating internal walls of a longitudinal cavity, the medical apparatus comprising:

a longitudinal sheath insertable in a working channel of an endoscopic device; and a positioning element comprising a first end connectable to the longitudinal sheath and having a central channel as well as a first guiding through-hole, a second end configured to be movable from the first end and from the longitudinal sheath and having a second guiding through-hole, and a deformable element fixable to at least the second end, wherein in a first configuration, the second end of the positioning element is at a first distance from the longitudinal sheath, the first guiding through-hole and the second guiding through-hole are aligned for receiving the treatment device, and the deformable element is compressed inside the longitudinal sheath, wherein in a second configuration, the second end of the positioning element is spaced apart from the longitudinal sheath at a second distance, wherein the first distance is different from the second distance, and wherein, in the second configuration, the deformable element is radially expanded, thereby touching, at least partially, the internal walls of the cavity so that (i) the first guiding through-hole and the second guiding through-hole are spaced apart from the internal walls of the cavity and (ii) when the treatment device inserted into the first guiding through-hole and the second guiding through-hole, the treatment device is moved towards and maintained at a position in a central region of the cavity.

2. The medical apparatus according to claim 1, wherein the first guiding through-hole is coaxial with the central channel and the second guiding through-hole is centered on the second end.

3. The medical apparatus according to claim 1, wherein:

a. the deformable element is configured to slide through the central channel of the first end so that, in the first configuration, the second end of the positioning element is in contact with the first end of the positioning element so that the first distance is smaller than the second distance and the deformable element is compressed inside the longitudinal sheath, or b. the deformable element is fixable also to the first end of the positioning element so that that, in the first configuration, the second end of the positioning element is moved away from the first end of the positioning element so that that the first distance is greater than the second distance and the deformable element is compressed outside the longitudinal sheath.

4. The medical apparatus according to claim 1, further comprising a distance varying element extending between the first end and the second end of the positioning element and fixable to the second end for reducing or increasing the distance between said first end and said second end when the positioning element passes from the first configuration to the second configuration and vice versa, the deformable element surrounding the distance varying element.

5. The medical apparatus according to claim 4, wherein:

a. the distance varying element is a tube-shaped element extending longitudinally from the first end to the second end and being slidably movable inside at least the longitudinal sheath and configured to receive the treatment device, wherein the first guiding through-hole and the second guiding through-hole are part of the distance varying element, or b. the distance varying element is a wire-shaped element extending longitudinally from the first end to the second end, wherein the wire-shaped element is slidably movable inside at least the longitudinal sheath.

6. The medical apparatus according to claim 1, further comprising an external sheath configured to contain both the longitudinal sheath and the treatment device, said external sheath being insertable in the working channel of the endoscopic device, the external sheath comprising a proximal inserting end and a distal end, wherein:

a. the proximal inserting end comprises a single port for the passage of the longitudinal sheath and of the treatment device, or b. the proximal inserting end comprises a first port for the passage of the longitudinal sheath and a second port for the passage of the treatment device, and/or c. the proximal inserting end comprises at least a luer-lock element, and/or d. the external sheath is made of a deformable material.

7. The medical apparatus according to claim 1, wherein the deformable element comprises a plurality of deformable threads, and wherein:

a. the plurality of deformable threads are made of a material having shape memory and superelasticity; and/or b. in the second configuration, the deformable element assumes a basket-shaped structure.

8. The medical apparatus according to claim 7, wherein the material having shape memory and superelasticity is a metal alloy of nickel and titanium.

9. The medical apparatus according to claim 1, further comprising an actuating element for causing the passage from the first configuration to the second configuration and vice versa, wherein one end of the deformable element is connectable to said actuating element, the actuating element being configured to slide along a direction of the longitudinal sheath.

10. The medical apparatus according to claim 1, wherein the medical apparatus has a longitudinal guiding axis (GA) passing through the first guiding through-hole and the second guiding through-hole, and wherein the passage from the first configuration to the second configuration causes a variation of the distance between said longitudinal guiding axis (GA) and the external walls of the cavity.

11. An ablating and resurfacing system for the ablation and the resurfacing of the superficial mucosae of a human cavity, the system comprising:

the medical apparatus according to claim 1, and a treatment device treating the internal walls of the human cavity, wherein, in the first configuration of the medical apparatus, the treatment device is extended through the first guiding through-hole and the second guiding through-hole, and wherein, in the second configuration of the medical apparatus, the second end of the positioning element is moved along the treatment device until the deformable element is expanded and the treatment device is moved away from the internal walls of the cavity towards a central region of the cavity.

12. The system according to claim 11, wherein:

a. the treatment device is a laser system emitting a radiation having a wavelength comprised between 1900 nm and 2100 nm or between 10200 nm and 10600 nm, and/or b. the treatment device is an optical fiber laser system comprising a laser generator coupled to an optical fiber structure having a tip portion for a diffusive or radial laser emission.

13. The system according to claim 11, further comprising a control unit, wherein the control unit is configured:

a. for controlling energy output of the treatment device when the treatment device is a laser system, or b. for controlling movement of the treatment device through the first guiding through-hole and the second guiding through-hole, or c. for controlling movement of the treatment device through the first guiding through-hole and the second guiding through-hole based on energy output of the treatment device when the treatment device is a laser system.

14. The system according to claim 11, wherein the treatment device extends longitudinally and is configured to slide along a direction of the longitudinal sheath through the first guiding through-hole and the second guiding through-hole when the medical apparatus is in the first configuration as well as in the second configuration.

15. An endoscopic device having at least a working channel and comprising the system according to claim 10, the system being insertable in the working channel of the endoscopic device.

16. A method for treating the internal walls of a human cavity by means of the system according to claim 11.

17. An endoscopic device having at least a working channel and comprising the medical apparatus according to claim 1, the medical apparatus being insertable in the working channel of the endoscopic device.

18. A method for treating the internal walls of a human cavity by means of the endoscopic device of claim 17.

19. A method for treating the internal walls of a longitudinal cavity, by means of the medical apparatus of claim 1.

20. The method according to claim 19, a. for treating a human cavity in the gastro intestinal system apparatus, with the purpose of targeting diseases of such apparatus, including Barrett's esophagus and other diseases and cancers formations, and/or b. for treating human cavities in the gastro intestinal apparatus, with the purpose of targeting metabolic diseases, in particular diabetes, nash, or fatty liver disease, and food intolerances.

21. The method according to claim 19 for treating a human cavity in the respiratory system, with the purpose of targeting respiratory diseases.

22. The method according to claim 19 for treating a human cavity in the cardiac system, with the purpose of targeting cardiac diseases.

23. The medical apparatus according to claim 1, wherein, in the first configuration, the deformable element is completely compressed in a radial direction of the longitudinal sheath.

24. The medical apparatus according to claim 1, wherein the central channel is spaced from the first guiding through-hole and the second guiding through-hole is not centered on the second end.

* * * * *